United States Patent [19]

Romano

[11] Patent Number: 5,393,556
[45] Date of Patent: Feb. 28, 1995

[54] COMPOSITION AND METHOD FOR DETECTING COUNTERFEIT PAPER CURRENCY

[76] Inventor: Camille Romano, 10964 SW. 71 La., Miami, Fla. 33173

[21] Appl. No.: 90,977

[22] Filed: Jul. 13, 1993

[51] Int. Cl.$^6$ ............................................. G01N 31/22
[52] U.S. Cl. ...................................... 427/7; 106/21 A; 106/21 C; 427/288; 427/384; 436/94
[58] Field of Search ............................ 427/7, 288, 386; 106/21 A, 21 K, 21 C; 436/94

[56] References Cited

U.S. PATENT DOCUMENTS

| | | | |
|---|---|---|---|
| 3,663,243 | 5/1972 | Stryker et al. | 106/21 A |
| 5,017,226 | 5/1991 | Kulisz | 106/21 A |
| 5,261,954 | 11/1993 | Collings | 106/21 A |

*Primary Examiner*—Janyce Bell
*Attorney, Agent, or Firm*—Ezra Sutton

[57] ABSTRACT

A composition for detecting the starch content in counterfeit paper currency comprising an aqueous-alcohol solution of iodine and acetic acid and method of applying same to paper currency genuine or counterfeit. In other embodiments, phenolthalien and bromine are included.

5 Claims, No Drawings

COMPOSITION AND METHOD FOR DETECTING COUNTERFEIT PAPER CURRENCY

FIELD AND HISTORICAL BACKGROUND OF THE INVENTION

The present invention is directed to a composition for detecting counterfeit paper currency and method for using such a composition.

It is well known that ever since paper currency was developed and put into use, the governments throughout the world have been concerned with the problem of counterfeiting. As the duplicating and printing, and especially the photocopying techniques have advanced over the years, it is more different than ever to distinguish between counterfeit and legitimate paper currency. It is obvious that the problem of counterfeiting paper currency is and has been a major concern of many governments around the world.

In response to the challenge of the ever growing concern of counterfeiting, instruments have been developed for detecting counterfeit currency. However, it has been discovered that known instruments are not reliable, or too expensive to manufacture. In some cases such instruments are to bulky and/or complex in design.

In the teachings of U.S. Pat. No. 5,063,163 an attempt has been made to provide a method of detecting counterfeit currency by assessing crudely the relative amounts of starch as a component of the paper used in the production of currency. As paper used in genuine currency is known to contain less sizing in form of starch while just the opposite is the case with regard to paper employed in the printing of counterfeit currency. It is well known that starch will react to dilute solutions of iodine. The reaction manifests in the production of a black coloration when starch is present while paper containing little or no starch will not appreciably discolor when a dilute iodine solution is applied to a selected spot on the paper.

The concept of applying iodine solution to paper containing starch as a sizing is well known. For instance, in Pulp and Paper Chemistry and Chemical Technology Third Edition Volume III by James P. Casey (1981) at page 1693, the author states as follows:

A qualitative test for starch in paper is based on the formation of a blue color when the paper is treated with iodine-potassium iodide solution."

at page 1894

"The presence of starch is indicated by the development of a blue color when a very dilute solution of iodine is placed on the surface of the paper."

It should be borne in mind that in most countries of the world it is illegal to deface currency by writing on it or deliberately staining it. In the teachings of U.S. Pat. No. 5,063,163 it is specifically stated that the solution forms a light golden brown coloration at the test area even though the paper currency being tested does not contain any starch.

OBJECTS AND SUMMARY OF THE INVENTION

The principal object of the present invention is to provide an improved composition and method of detecting counterfeit paper currency which is reliable and does not require the use of expensive, bulky and complex equipment and procedure. The improved composition does not color or deface the genuine currency. Furthermore, no preselected standard need be selected for comparison purposes as called for in issued U.S. Pat. No. 5,063,163.

The improved composition comprises an aqueous-alcohol iodine solution which has been acidified with acetic acid as the preferred embodiment. Other ingredients may be added such as a phenolthalien for testing the pH of the paper and bromine may be included.

The preferred improved formulation is as follows:

| | |
|---|---|
| Potassium iodide crystals | 0.4% by weight |
| Iodine crystals | 0.2% by weight |
| Water to triturate | 5.0 ml |
| Acetic acid (glacial) | 1.2 ml |
| Ethyl alcohol (75%) | QS to 100 ml. |

It is submitted that various percentages of the noted ingredients may be altered in order to provide various test solutions of varying strengths. In any event the main component of the test solution is the iodine element.

As another embodiment phenothalien in the range of 0.15% to 0.25% by weight is included in order to test the pH of the various genuine currencies of the world some of which will be alkaline and some will be acidic.

Such a formulation is as follows:

| | |
|---|---|
| Potassium iodide crystals | 0.4% by weight |
| Iodine crystals | 0.2% by weight |
| Phenolthalien | 0.2% by weight |
| Water to triturate | 5.0 ml |
| Ethyl alcohol | QS to 100 ml. |

In another embodiment bromine solution in the range of 0.05% to 0.15% by weight is included as a bleachant to produce another embodiment:

| | |
|---|---|
| Potassium iodide crystals | 0.4% by weight |
| Iodine crystals | 0.2% by weight |
| Bromine | 0.1% by weight |
| Water to triturate | 5.0 ml |
| Ethyl alcohol | Q.S. to 100 ml |

Other ingredients may be included as desired. For instance other alkyl alcohols may be employed.

The test solution may be dispensed in small quantities from containers of varying sizes, and can be applied by any known method, such as by using a dropper or the like device. Alternatively solution may also be dispensed from the reservoirs of pen-like writing instruments for quick and easy application. Other suitable methods or devices may also be employed for dispensing and easy application of the test solution.

The method of use of the improved formulation includes applying the test solution to a small test area of paper currency. If the currency is a genuine paper currency no color change of the test solution area will be observed, assuming, of course, that the genuine paper currency does not contain starch. On the other hand, in the case of a counterfeit currency which will probably contain starch, the color of the test area of the counterfeit currency will change from any initial color to bluish-black or even substantially black.

As stated, it is believed that the iodine in the test solution reacts with the starch content in the counterfeit paper currency to form a bluish-black or substantially black complex. On the other hand, the genuine paper currency, either does not contain any starch, or its content is chemically untraceable, and therefor, iodine in the test solution remains unreacted and no color change is observed.

Once standards as to whether a genuine paper currency domestic or foreign has been determined to be either acidic or alkaline, the inclusion of the phenolthalien in an otherwise neutral iodine containing test solution of the instant invention will give information as to whether the to-be-tested currency is acidic or alkaline, thereby corresponding or not corresponding with the genuine currency. A reading to the contrary as to what is expected of that particular currency along with a reading as to the presence or non-presence of starch will give an additional parameter as to whether the currency is genuine or counterfeit if the test site differs from what is expected.

The presence of bromine in one of the embodiments provides a bleachant to assist in avoiding untoward discoloration of the currency, certainly not desirable if the currency is genuine.

While this invention has been described as having a preferred embodiments, it is understood that it is capable of further modifications, uses and/or adaptations of the invention and following in general the principles of the invention and including such departure from the present disclosure as come within known or customary practice in the art to which the present invention pertains, and as may be applied to central features hereinbefore set forth, and fall within the scope of the invention or the limits of the claims appended hereto.

What is claimed is:

1. A composition for detecting the starch content in paper currency comprising an aqueous-alcohol solution of iodine and phenolthalien.

2. The composition of claim 1 including bromine.

3. The method of detecting the presence of starch in paper currency including applying a quantity of the composition of claim 2 to said paper currency and observing any change in color.

5. The method of detecting the presence of starch in paper currency including applying a quantity of the composition of claim 1 to said paper currency and observing any change in color.

4. The composition of claim 1 wherein the alcohol is ethyl alcohol.

* * * * *